(12) United States Patent
Hosoi

(10) Patent No.: US 7,138,232 B2
(45) Date of Patent: *Nov. 21, 2006

(54) STIMULABLE PHOSPHOR SHEET FOR DETECTION OF SUBSTANCES ORIGINATING FROM LIVING BODY OR ITS ANALOGUES

(75) Inventor: Yuichi Hosoi, Kanagawa (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 356 days.

This patent is subject to a terminal disclaimer.

(21) Appl. No.: 10/154,925

(22) Filed: May 28, 2002

(65) Prior Publication Data
US 2002/0177156 A1 Nov. 28, 2002

(30) Foreign Application Priority Data
May 25, 2001 (JP) ............................. 2001-157462

(51) Int. Cl.
*C11Q 1/68* (2006.01)
*C12M 1/36* (2006.01)
*C07H 21/04* (2006.01)
*G08F 15/00* (2006.01)

(52) U.S. Cl. .................. 435/6; 435/174; 435/283.1; 435/287.2; 536/23.1; 536/24.31

(58) Field of Classification Search .................. 435/6, 435/174, 283.1, 287.2, 288.4; 536/23.1; 422/68.1, 82.01
See application file for complete search history.

(56) References Cited

U.S. PATENT DOCUMENTS 5,055,681 A * 10/1991 Tsuchino et al. ............ 250/585
6,236,744 B1 * 5/2001 Some et al. ................ 382/132
6,255,660 B1 * 7/2001 Isoda et al. ............... 250/484.4

* cited by examiner

Primary Examiner—BJ Forman
(74) Attorney, Agent, or Firm—Sughrue Mion, PLLC

(57) ABSTRACT

A method employing a porous material sheet which has at predetermined positions plural dots each being composed of a group of probe molecules and a stimulable phosphor sheet having a phosphor layer which contains a stimulable phosphor in an amount of 10 to 140 g/m² is favorably utilized to detect by autoradiography radioactively labeled substances originating from living body or its analogues which are able to be fixed to the probe molecules by biochemically specific binding reaction.

5 Claims, 3 Drawing Sheets

STIMULABLE PHOSPHOR SHEET FOR DETECTION OF SUBSTANCES ORIGINATING FROM LIVING BODY OR ITS ANALOGUES

FIELD OF THE INVENTION

The present invention relates to a method for detecting substances originating from living body or analogues thereof according to biochemically specific binding reaction. In particular, the invention relates to an improved method utilizing a porous sheet and a stimulable phosphor sheet in combination.

BACKGROUND OF THE INVENTION

Recently, analytical elements such as a macro-array sheet and a micro-array sheet are widely utilized in gene analysis technology in the biological and medical fields. These analytical elements are used to analyze nucleic acids such as DNA and RNA, their fragments, and their duplicates such as PCR products. The analysis is performed by detecting the nucleic-acids utilizing hybridization, which is one of biochemically specific binding reaction. The former macro-array sheet is made of porous sheet of polyamide resin or the like. For the analysis using the macro-array sheet, a large number of nucleic acid fragments (probe molecules) such as DNA fragments are first fixed to the porous sheet by entanglement. The binding reaction is carried out using (target) sample nucleic acid fragments labeled with radio-isotope (RI). The latter micro-array is composed of solid carrier such as surface-treated slide glass plate. For the analysis using the micro-array sheet, the probe molecules are first fixed to the surface of the solid carrier. The binding reaction is carried out between the probe molecules and sample nucleic acid fragments labeled with fluorescent compound.

However, the names of macro-array sheet and micro-array sheet are not always employed distinctly to mean each of the above-described analytical elements.

The gene analysis utilizing a macro-array sheet is advantageous because it can be carried out using the conventional autoradiography.

The conventional procedures for detecting a nucleic acid such as DNA are generally conducted by the process comprising the following steps:

(1) preparing a number of single-stranded nucleic acid fragments (probe molecules: generally employed are those of which base sequences are already known); spotting in series an aqueous solution containing the fragments on a macro-array sheet using a spotter so that a large number of spots can be densely placed on the sheet to form a matrix composed of pores to which probe molecules are fixed by entanglement, whereby a large number of probe molecule spots in the form of dots are produced;

(2) bringing single-stranded sample nucleic acid fragments (to be analyzed) with a radioisotope label (RI, for instance, $^{32}P$ and $^{33}P$) contained in an aqueous solution into contact with the macro-array sheet (for instance, by immersing the macro-array sheet in an aqueous solution of the radioisotope-labeled sample nucleic acid fragments placed in a specific vessel) to fix target nucleic acid fragments to the macro-array sheet by hybridization with the probe molecules; namely, the target complementary nucleic acid fragments in the sample nucleic acid fragments are bound to the probe molecules in the spot by hybridization;

(3) removing unfixed radioisotope-labeled sample nucleic acid fragments from the macro-array sheet by washing;

(4) drying and placing the macro-array sheet on a radiographic film for detecting radiation coming from the radioisotope-labeled target nucleic acid fragments by autoradiography, whereby the binding information of the fixed target nucleic acid fragments (for instance, presence and amount of fixed fragments) are obtained; and (5) determining at least local base sequence information of the target nucleic acid fragments according to complementation principle, in the case that the base sequence of the probe molecules is previously known.

Thus, a large number of genes are simultaneously analyzed in their expression, mutation, and polymorphism, utilizing the above-described technology.

Recently, a radiation image recording and reproducing method utilizing a radiation image storage panel (which is also named "imaging plate" or "stimulable phosphor sheet") has been developed for performing autoradiography of radioisotope-labeled biological specimen and polymers originating from living body, in place of the conventional autoradiography using a radiographic film.

The radiation image recording and reproducing method utilizes stimulable phosphor (i.e., radiation image storage phosphor) which absorbs and stores radiation energy when it is exposed to radiation such as X rays, and thereafter produces emission in an amount proportional to the stored radiation energy when it is irradiated with electromagnetic wave (stimulating light) such as visible light or infrared rays, and is generally carried out by a procedure of the following steps:

applying to a stimulable phosphor sheet containing stimulable phosphor a radiation transmitted through or emitted by a target subject, whereby recording the radiation image in the phosphor sheet;

scanning sequentially the phosphor sheet with a stimulating light such as laser light, whereby the phosphor sheet sequentially produces stimulated emission;

photoelectrically detecting the stimulated emission to obtain a series of electric image signals (digital signals); and storing in an appropriate recording means the digital signals as such or after being subjected to various image processings for forming a visible image.

The autoradiography according to the above-described radiation image recording and reproducing method which utilizes a stimulable phosphor sheet is considered to be important autoradiographic technology, because it has various advantageous features, for instance, it gives a radiation image with high sensitivity even if the amount of radiation coming from the radioisotope-labeled specimen is extremely small, and it gives an image information of digital data which is easily subjected to various image processing procedures and is easily stored.

The autoradiographic procedure utilizing the stimulable phosphor sheet for measuring radiation coming from radioisotope-labeled target molecules is already reported. For instance, Human Molecular Genetics, 1999, Vol. 8, No. 9, 1715–1722 describes that a target molecule can be detected by the steps of producing a large number of spots of DNA fragments (probe molecules) on a porous sheet, hybridizing radioisotope-labeled sample DNA fragments complementary to the probe molecules on the porous sheet, and carrying out the autoradiographic process by placing the porous sheet on a stimulable phosphor sheet.

The gene analysis utilizing a porous sheet such as a macro-array sheet enables to detect radioisotope-labeled target molecules with a high sensitivity when an autoradiographic process is performed utilizing the stimulable phosphor sheet.

It has been noted by the inventor, however, that a stimulable phosphor sheet having a stimulable phosphor layer of approx. 200 to 400 μm thick which has been generally employed for radiographic clinical examination as well as a stimulable phosphor sheet having a stimulable phosphor layer of approx. 50 to 200 μm thick which has been generally employed for conventional autoradiography are not appropriate for obtaining a reproduced radiation image with high resolution in the autoradiographic gene analysis using a macro-array sheet.

SUMMARY OF THE INVENTION

Further studies by the inventor have revealed that the radioisotopes such as $^{32}$P, $^{33}$P and $^{35}$S which are generally employed for autoradiography of gene analysis or analysis of substances originating from living body or its analogues are contained in the substances in an extremely small amount, and their radiation energy is very weak. It has been furthermore discovered that approximately 90% or more of the radiation energy applied on the surface of the stimulable phosphor layer is absorbed in the phosphor layer within a depth of 50 μm from the surface. Accordingly, in the autoradiographic gene analysis, a stimulable phosphor layer having a thickness of larger than 50 μm is unfavorably employed, because the phosphor portion of deeper than the 50 μm depth not only does not work to increase sensitivity but also gives adverse effect to the quality of radiation image owing to lowering of resolution.

The present invention has an object to provide a method or process for detecting substances originating from living body or analogues thereof with high resolution, preferably with low noise.

The present invention resides in a method employing a porous material sheet which has at predetermined positions plural dots each comprising a group of probe molecules and a stimulable phosphor sheet having a phosphor layer which contains a stimulable phosphor in an amount of 10 to 140 g/m$^2$, to detect by autoradiography radioactively labeled substances originating from living body or its analogues which are able to be fixed to the probe molecules by biochemically specific binding reaction.

The invention further resides in a laminate of a stimulable phosphor sheet having a phosphor layer which contains a stimulable phosphor in an amount of 10 to 140 g/m$^2$ and a porous material sheet which has at predetermined positions plural dots each comprising a group of probe molecules and radioactively labeled substances originating from living body or its analogues which are fixed to the probe molecules by biochemically specific binding reaction.

The invention further resides in a process for detecting complementary nucleic acid fragments which comprises the steps of:

preparing a porous material sheet which has at predetermined positions plural dots each comprising a group of probe molecules;

bringing sample substances originating from living body or its analogues having a radioactive label in a liquid phase into contact with the prepared porous material sheet, whereby target substances in the sample substances are fixed to the probe molecules by biochemically specific reaction;

removing unfixed sample substances from the porous material sheet;

keeping the last-mentioned porous material sheet in contact with a stimulable phosphor sheet having a phosphor layer which contains a stimulable phosphor in an amount of 10 to 140 g/m$^2$, whereby the stimulable phosphor layers absorbs and stores radiation energy of the radioactive label coming from the fixed target substances;

irradiating the stimulable phosphor sheet with a stimulating light, whereby the phosphor layer in which the radiation energy is stored releases stimulated emissions;

detecting the stimulated emissions photoelectrically to obtain a series of electric signals; and processing the electric signals to detect dots in which the target substances are present.

The invention furthermore resides in a process for detecting complementary nucleic acid fragments which comprises the steps of:

preparing a composite material sheet which comprises partitions two-dimensionally extending on a sheet plane to form on the sheet plane plural fine sections surrounded by the partitions and porous material portions each of which is placed in the fine section, to each porous material portion of which a group of probe molecules are attached;

bringing sample substances originating from living body or its analogues having a radioactive label in a liquid phase into contact with the prepared composite material sheet, whereby target substances in the sample substances are fixed to the probe molecules by biochemically specific reaction;

removing unfixed sample substances from the composite material sheet;

keeping the last-mentioned composite material sheet in contact with a stimulable phosphor sheet having a phosphor layer which contains a stimulable phosphor in an amount of 10 to 140 g/m$^2$, whereby the stimulable phosphor layer absorbs and stores radiation energy of the radioactive label coming from the fixed target substances;

irradiating the stimulable phosphor sheet with a stimulating light, whereby the stimulable phosphor layer in which the radiation energy is stored releases stimulated emissions;

detecting the stimulated emissions photoelectrically to obtain a series of electric signals; and processing the electric signals to detect dots in which the target substances are present.

Preferred embodiments of the invention are described below.

(1) The phosphor layer has a thickness of 5 to 50 μm.

(2) The probe molecules are nucleic acid fragments, and the substances originating from living body or its analogues are nucleic acid fragments complementary to the probe molecules.

(3) The probe molecules are single-stranded nucleic acid fragments and the substances originating from living body or its analogues are single-stranded nucleic acid fragments complementary to the probe molecules.

(4) The radioactive label is a label of isotope selected from the group consisting of $^{32}$P, $^{33}$P and $^{35}$S.

(5) The partitions of the composite material sheet are made of material having a mean density of not lower than 0.6 g/cm$^3$ and the porous material portions have a mean density of not higher than 1.0 g/cm$^3$, provided that the mean density of material of the partitions is higher than the mean density of the material of the porous material portions.

(6) At least one of upper and lower surfaces of the porous material portions in the composite material sheet is retracted-from the upper or lower surface of the adjoining partitions on the sheet plane.

(7) The difference between the mean density of material of the partitions and the mean density of the porous material portions of the composite material sheet is not less than 0.1 g/cm³, preferably not less than 0.5 g/cm³, more preferably not less than 1.0 g/cm³.

(8) The mean density of material of the partitions is in the range of 1 to 20 g/cm³, preferably 2 to 10 g/cm³.

(9) The mean density of the porous material portions of the composite material sheet is in the range of 0.1 to 0.5 g/cm³.

(10) The partitions of the composite material sheet are made of metal, plastic material, or ceramics, preferably nickel metal or nickel alloy.

(11) The porous material portions of the composite material sheet are made of porous organic polymer material, preferably porous polyamide or porous cellulose derivatives.

(12) The fine sections of the composite material sheet which have therein the porous material portion therein have an opening whose mean area is smaller than 5 mm², preferably smaller than 1 mm², more preferably smaller than 0.1 mm², and larger than 0.001 mm², preferably larger than 0.01 mm².

(13) The fine sections having the porous material portion therein are produced in numbers per cm² (density) of not less than 10, preferably not less than 100, more preferably not less than 1,000, and not more than 100,000, more preferably not more than 10,000.

DETAILED DESCRIPTION OF THE INVENTION

The stimulable phosphor sheet, and a laminate of the stimulable phosphor sheet and a porous material sheet (or a composite material sheet) employed in the autoradiography of the invention are described by referring to the attached drawings.

Figure 1:
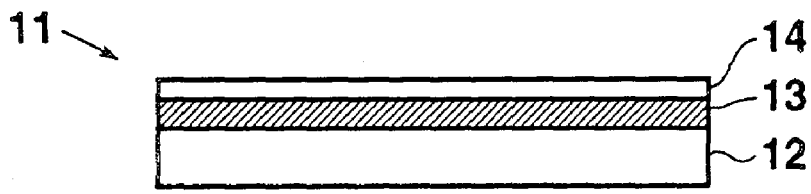
FIG. 1 is a sectional view of a stimulable phosphor sheet employed in the invention.

FIG. 1 shows a section of a typical stimulable phosphor sheet. In FIG. 1, the stimulable phosphor sheet 11 is composed of a support 12, a phosphor layer 13 containing stimulable phosphor, and a protective layer 14. In the phosphor layer 13, the stimulable phosphor is contained in an amount of 10 to 140 g/m², preferably 15 to 70 g/m². The phosphor layer preferably has a thickness of 5 to 50 μm, more preferably 5 to 45 μm, more preferably 5 to 35 μm.

If the radioisotope to be employed for labeling the target substances are one of the following radioisotopes (RI):

$^{32}P$ (maximum energy: 1.709 MeV)
$^{33}P$ (maximum energy: 0.249 MeV)
$^{35}S$ (maximum energy: 0.167 MeV)

90% or more of the radiation emitted by RI is absorbed in the phosphor layer within the 50 μm depth. Accordingly, a radiation image is recorded in the phosphor layer without lowering resolution.

The substrate and/or protective layer can be omitted from the stimulable phosphor sheet. A stimulable phosphor sheet having no substrate or no protective layer can be favorably employed for autoradiography, because the phosphor layer can be directly placed in touch with the porous material sheet when autoradiography is performed.

Figure 2:
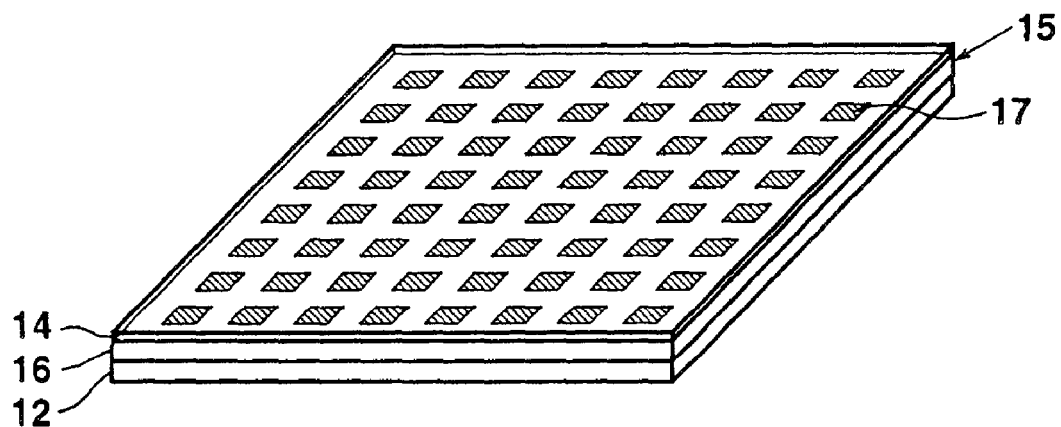
FIG. 2 is a schematic view of another stimulable phosphor sheet employed in the invention.
Figure 3:
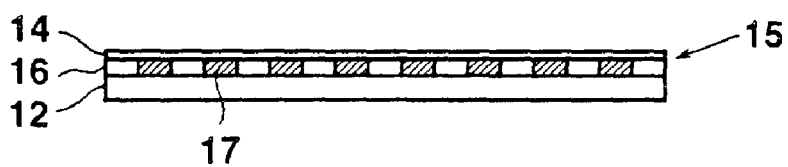
FIG. 3 is a section of the stimulable phosphor sheet of FIG. 2 taken out along the line I—I.

The stimulable phosphor sheet can be that illustrated in FIG. 2 and FIG. 3.

The stimulable phosphor sheet of FIGS. 2 and 3 comprises a support sheet and finely divided stimulable phosphor layers which are distributed on the support in such manner that each stimulable phosphor layer takes a position corresponding to each fine section of the composite material sheet or to each position in which a sample molecule solution is to be spotted.

In FIGS. 2 and 3, the stimulable phosphor sheet is illustrated, respectively, by schematic view and sectional view. In FIGS. 2 and 3, the stimulable phosphor sheet 15 is composed of a support 12 and a phosphor layer 16 comprising plural stimulable phosphor layers 17 in the form of dots which are produced on the support 12 separately. On the phosphor layer, a protective layer 14 is placed.

In the stimulable phosphor sheet, the plural stimulable phosphor layers 17 in the form of dots are preferably isolated from each other by high density partitions (for instance, having a density of not less than 0.6 g/cm³) so that radiation energy in one dot does not penetrate the surrounding partitions. It is noted that the stimulable phosphor layers may be placed on the support uniformly or locally.

As described hereinbefore, the stimulable phosphor is contained in an amount of 10 to 140 g/m², preferably 15 to 70 g/m². The phosphor layer preferably has a thickness of 5 to 50 μm, more preferably 5 to 45 μm, more preferably 5 to 30 μm.

As the stimulable phosphor, a phosphor giving a stimulated emission of a wavelength in the region of 300 to 500 nm when it is irradiated with stimulating rays of a wavelength in the region of 400 to 900 nm is preferably employed. In Japanese Patent Provisional Publications No. 2-193100 and No. 4-310900, some examples of the stimulable phosphors are described in detail. Examples of the preferred stimulable phosphors include divalent europium or cerium activated alkaline earth metal halide phosphors (e.g., BaFBr:Eu, BaF(BrI):Eu), and cerium-activated oxyhalide phosphors.

Most preferred stimulable phosphors are rare earth metal activated alkaline earth metal fluorohalide phosphors having the following essential formula (I):

$$M^{II}FX{:}zLn \qquad (I)$$

in which $M^{II}$ is an alkaline earth metal such as Ba, Sr, or Ca; Ln is a rare earth-metal such as Ce, Pr, Sm, Eu, Tb, Dy, Ho, Nd, Er, Tm, or Yb; X is a halogen atom such as Cl, Br, or I; and z is a value satisfying the condition of $0 < z \leq 0.2$.

$M^{II}$ of the formula (I) preferably comprises Ba in an amount of 50 atomic % or more. Ln preferably is Eu or Ce. It should be noted that the formula (I) does not mean F:X=1:1, but means to have a crystalline structure of BaFX. Thus, the formula (I) does not accurately indicate stoichiometric amounts of the constitutional elements. It is generally preferred that F is slightly rich in comparison with X, because $F^+$ center ($X^-$ center) produced in such composition efficiently gives a stimulated emission when the phosphor is stimulated with a light in the region of 600 to 700 nm.

The stimulable phosphor of the formula (I) can further contain one or more of the following additive components:

bA, $wN^I$, $xN^{II}$, $yN^{III}$

In the above formulas, A is a metal oxide such as $Al_2O_3$, $SiO_2$ or $ZrO_2$, in which source of the metal oxide preferably is extremely fine particles having a mean diameter (of primary particles) of 0.1 μm or less and has little reactivity to $M^{II}FX$ particles to keep the $M^{II}FX$ particles from coagulation; $N^I$ is a compound of an alkali metal such as Li, Na, K, Rb, or Cs; $N^{II}$ is a compound of an alkaline earth metal such as Mg and/or Be; and $N^{III}$ is a compound of a monovalent or trivalent metal such as Al, Ga, In, Tl, Sc, Y, La, Gd, or Lu. The metal compounds preferably are halide compounds such as those described in Japanese Patent Provisional Publication No. 59-75200.

In the formulas, each of b, w, x, and y is a value which means an amount of each source material, based on one molar amount of $M^{II}FX$, under the conditions of $0 \leq b \leq 0.5$, $0 \leq w \leq 2$, $0 \leq x \leq 0.3$, and $0 \leq b \leq 3$. Accordingly, the value of b, w, x, or y does not necessarily mean the amount of each element or compound existing in the finally produced phosphor. Further, each additive compound may exist as such in the finally produced phosphor or may react with $M^{II}FX$ in the course of the preparation of the stimulable phosphor.

Furthermore, the stimulable phosphor of the formula (I) may contain one or more of the following compounds or reaction products thereof:

Compounds of Zn and Cd described in Japanese Patent Provisional Publication No. 55-12145;

Metal oxides such as $TiO_2$, BeO, MgO, CaO, SrO, BaO, ZnO, $Y_2O_3$, $La_2O_3$, $In_2O_3$, $GeO_2$, $SnO_2$, $Nb_2O_5$, $Ta_2O_5$, and $ThO_2$ described in Japanese Patent Provisional Publication No. 55-160078;

Compounds of Zr and Sc described in Japanese Patent Provisional Publication No. 56-116777;

Compounds of B described in Japanese Patent Provisional Publication No. 57-23673;

Compounds of As and Si described in Japanese Patent Provisional Publication No. 57-23675;

Tetrafluoroborate compounds described in Japanese Patent Provisional Publication No. 59-27980;

Hexafluoro compounds such as monovalent or divalent salts of hexafluorosilicic acid, hexafluorotitanic acid, or hexafluorozirconic acid described in Japanese Patent Provisional Publication No. 59-47289; and Compounds of transitional metals such as V, Cr, Mn, Fe, Co, and Ni described in Japanese Patent Provisional Publication No. 59-56480.

Moreover, other additives may be incorporated, provided that the incorporated additives do not disturb the preparation of the essential phosphor composition of the formula (I).

The rare earth activated alkaline earth metal fluorohalide phosphors of the formula (I) generally have an aspect ratio of 1.0 to 5.0. The stimulable phosphor particles favorably employed for the production of the stimulable phosphor sheet of the invention have an aspect ratio of 1.0 to 2.0, more preferably 1.0 to 1.5. The particle size preferably is in the range of 1 μm to 10 μm, more preferably 2 μm to 7 μm, in terms of Median diameter (Dm), and σ/Dm (σ is a standard deviation of the particle size distribution) preferably is not more than 50%, more preferably not more than 40%. The particles may be in the form of parallelepiped, regular hexahedron, regular octahedron, tetradecahedron, intermediate polyhedron, or amorphous. The phosphor particles of tetradecahedron are preferred.

Examples of the binders include natural polymers such as proteins (e.g., gelatin), polysaccharides (e.g., dextran) and gum arabic; and synthetic polymers such as polyvinyl butyral, polyvinyl acetate, nitrocellulose, ethyl cellulose, vinylidene chloride-vinyl chloride copolymer, polyalkyl (meth)acrylate, vinyl chloride-vinyl acetate copolymer, polyurethane, cellulose acetate butyrate, polyvinyl alcohol, linear polyester, and thermoplastic elastomers. The polymer material may be crosslinked.

The stimulable phosphor particles and binder are placed in an appropriate solvent to prepare a dispersion. The ratio of binder and stimulable phosphor particles in the phosphor dispersion generally is in the range of 1:1 to 1:100 (binder: phosphor, by weight), preferably 1:8 to 1:40.

The phosphor dispersion is coated on a support such as glass plate, metal plate, or plastic sheet, and dried to give a phosphor layer.

The stimulable phosphor sheet also can have a light-reflective layer on one surface side (or between the phosphor sheet and the support, if the support is provided), so as to increase the sensitivity of the phosphor sheet.

As the support, a sheet or a film of flexible resin material having a thickness of 50 μm to 1 mm is generally employed. The support may be transparent or may contain light-reflecting material (e.g., alumina particles, titanium dioxide particles, and barium sulfate particles) or voids, for reflecting the stimulating rays or the stimulated emission. Further, it may contain light-absorbing material (e.g., carbon black) for absorbing the stimulating rays or the stimulated emission. Examples of the resin materials include polyethylene terephthalate, polyethylene naphthalate, aramid resin and polyimide resin. The support may be a sheet of other material such as metal, ceramics and glass, if needed. On the phosphor sheet-side surface of the support, auxiliary layers (e.g., light-reflecting layer, light-absorbing layer, adhesive layer, electroconductive layer) or many hollows may be provided. On the other side surface, a friction-reducing layer or an anti-scratch layer may be formed.

On the surface not facing the support, the stimulable phosphor sheet may have a protective cover film. In order not to affect the stimulating rays or the stimulated emission, the cover film preferably is transparent. Further, for efficiently protecting the stimulable phosphor sheet from chemical deterioration and physical damage, the protective film should be both chemically stable and physically strong.

The cover film (or protective layer) can be provided by fixing a beforehand prepared transparent plastic film (e.g., polyethylene terephthalate) on the stimulable phosphor sheet with adhesive, or by coating the phosphor sheet with a solution of cover film material and drying the coated solution. Into the cover film, fillers of fine particles may be incorporated so as to reduce blotches caused by interference and to improve the quality of the resultant radiation image. The thickness of the cover film generally is in the range of approx. 0.1 to 20 μm.

For enhancing the resistance to staining, a fluororesin layer is preferably provided on the cover film. The fluororesin layer can be formed by coating the surface of the cover film with a solution of a fluororesin in an organic solvent, and drying the coated solution. The fluororesin may be used singly, but generally a mixture of the fluororesin and a film-forming resin is employed. In the mixture, an oligomer having polysiloxane structure or perfluoroalkyl group can be further added. Into the fluororesin layer, a filler of fine particles may be incorporated so as to reduce blotches caused by interference and to improve quality of the resultant radiation image. The thickness of fluororesin layer generally is in the range of 0.5 to 20 μm. In the formation of the fluororesin layer, additives such as a crosslinking agent, a film-hardening agent and an anti-yellowing agent can be used. In particular, the crosslinking agent advantageously improves durability of the fluororesin layer.

The light-reflective layer can comprise a white pigment such as alumina pigment, titanium dioxide pigment, or a barium sulfate pigment, or phosphor particles giving no stimulated emission. In the light-reflective layer, the pigment or particles are dispersed and supported in a binder.

The stimulable phosphor layer can be formed on the support by vapor deposition.

A particularly preferred stimulable phosphor for vapor deposition is an alkali metal halide phosphor having the following formula (II):

$$M^I X . a M^{II} X'_2 . b M^{III} X''_3 : zA \quad \text{(II)}$$

in which $M^I$ is at least one alkali metal element selected from the group consisting of Li, Na, K, Rb and Cs; $M^{II}$ is at least one alkaline earth metal element or divalent metal element selected from the group consisting of Be, Mg, Ca, Sr, Ba, Ni, Cu, Zn and Cd; $M^{III}$ is at least one rare earth element or trivalent metal element selected from the group consisting of Sc, Y, La, Ce, Pr, Nd, Pm, Sm, Eu, Gd, Tb, Dy, Ho, Er, Tm, Yb, Lu, Al, Ga and In; A is at least one rare earth element or metal element selected from the group consisting of Y, Ce, Pr, Nd, Sm, Eu, Gd, Tb, Dy, Ho, Er, Tm, Yb, Lu, Na, Mg, Cu, Ag, Tl and Bi; each of X, X' and X" independently is at least one halogen selected from the group consisting of F, Cl, Br and I; and a, b and z are numbers satisfying the conditions of $0 \leq a < 0.5$, $0 \leq b < 0.5$ and $0 \leq z < 0.2$, respectively.

In the formula (II), at least Cs is preferably included as $M^I$, at least Br is preferably included as X, and A is particularly preferably Eu or Bi. The phosphor of the formula (II) may contain a metal oxide (such as aluminum oxide, silicon dioxide or zirconium oxide) as an additive in an amount of not more than 0.5 mol based on 1 mol of $M^I$.

The phosphor layer can be formed by electron beam-evaporating method, which belongs to the vapor accumulation method. The electron beam-evaporating method gives regularly aligned prismatic crystals having good shape. Further, since the vapor source is locally heated and instantly vaporized, the composition of the resultant phosphor in the layer is usually almost the same as that of the phosphor of the vapor source. In contrast, in other vapor accumulation methods, since a component having a high vapor pressure is preferentially vaporized (for example, an activator is vaporized prior to the phosphor matrix components), the composition of the resultant phosphor may be not coincident with that of the phosphor of the vapor source.

In the first place, a stimulable phosphor of vapor source and a substrate on which the vapor is to be deposited are set in an vapor-deposition apparatus. The apparatus is then evacuated to give a pressure of $3 \times 10^{-10}$ to $3 \times 10^{-12}$ kg/cm². The substrate is placed perpendicularly to the direction in which the vapor comes out of the source. Inert gases such as Ar and Ne may be introduced into the apparatus while the vacuum is kept in the above range.

In the second place, an electron beam generated by an electron gun is applied onto the vapor source. The accelerating voltage of electron beam is preferably in the range of 1.5 kV to 5.0 kV. If it is lower than 1.5 kV, the voltage is so unstable that the beam position drifts. Further, since the surface of vapor source scanned by the electron beam is deformed, the vaporizing surface can not be kept flat. If the accelerating voltage is higher than 5.0 kV, the prismatic phosphor crystals grow unevenly in a gas phase by vaporization.

By applying the electron beam, the stimulable phosphor of vapor source is heated, scattered and deposited on the substrate. The deposition rate of the phosphor is generally in the range of 0.1 to 1,000 μm/min., preferably in the range of 1 to 100 μm/min. The electron beam may be applied twice or more to form two or more phosphor layers. Further, two or more phosphors may be co-deposited by means of plural electron guns. It is also possible that the phosphor layer be formed on the substrate simultaneously with synthesizing the phosphor from materials. The substrate may be cooled or heated, if needed, during the deposition process, or may be subjected to heat treatment (annealing treatment) after the deposition process is complete.

The composite material sheet favorably employed in the invention comprises partitions which extend two-dimensionally on the sheet to divide the sheet to give a large number of fine sections and a corresponding large number of porous material portions placed in the fine sections.

The structure of the composite material sheet is explained by referring to the attached drawings.

Figure 4:
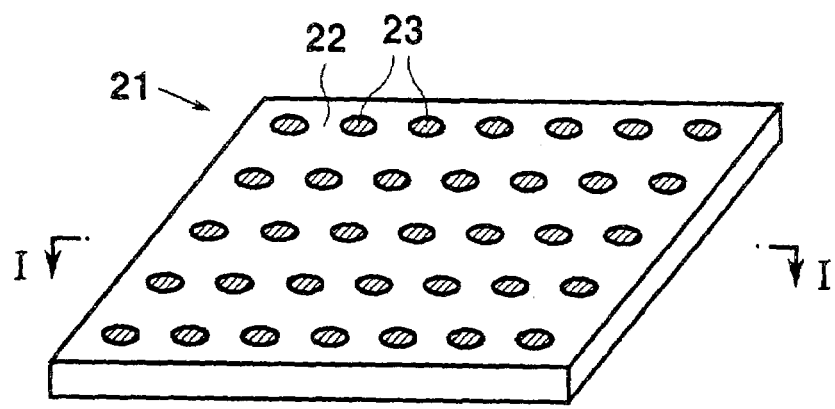
FIG. 4 is a schematic view of a composite material sheet employable in the invention.
Figure 5:
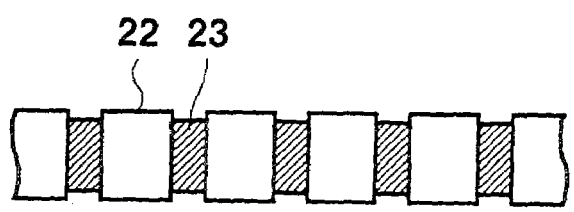
FIG. 5 is an enlarged view of the section taken out along I—I line of FIG. 1.

FIG. 4 is a schematic view of the composite material sheet according to the invention, and FIG. 5 is an enlarged view of the section taken out along I—I line of FIG. 4.

In FIGS. 4 and 5, the composite material sheet 21 is composed of partitions 22 giving a large number of through-holes and porous material portions (i.e., porous structure portions: shadow area) 23 enclosed with the partitions 22. The porous material portions 23 are placed within the small through-holes. The opening of the through-hole generally has an area of smaller than 5 mm², preferably smaller than 1 mm², more preferably smaller than 0.1 mm², and larger than 0.001 mm², preferably larger than 0.01 mm².

It is preferred that at least one of the upper surface and lower surface of the porous material portion 23 is retracted from the upper surface and lower surface of the adjoining partitions. Such structure of the porous material portion enables to receive spotting of a probe solution and prohibits overflow of the spotted solution onto the adjoining porous material portions.

The fine sections in each of which the porous material portion is placed are generally produced in numbers per cm² (i.e., density) of not less than 10, preferably not less than 100, more preferably not less than 1,000, but not more than 100,000, more preferably not more than 10,000. The fine sections are not always provided at equal spaces. Plural groups of fine sections are separately located on the sheet.

The partitions 22 have a mean density of not less than 0.6 g/cm³ preferably in the range of 1 to 20 g/cm³, more preferably in the range of 2 to 10 g/cm³ so that the partitions can efficiently shield transmission of radiation such as electron rays. It is known that the distance of transmission of radiation is inversely proportional to the density of material. Therefore, if the radioisotope (RI) is ordinary one such as $^{32}P$, $^{33}P$ or $^{35}S$, the partition having such mean density can effectively shield transmission of radiation therethrough, and protects a reproduced radiation image from lowering of resolution.

Examples of material of the partition having such area mean density include metal such as nickel or nickel alloy, plastic material such as polyamide resin, aramid resin, polyethylene terephthalate resin, polyolefin resin (e.g., polyethylene resin or polypropylene resin); and ceramics such as alumina, zirconia, magnesia, and quartz.

The porous material portions 23 of the composite material sheet to which probe molecules such as nucleic acids, its fragments, synthesized oligonucleotides are fixed have a mean density of not higher than 1.0 g/cm$^3$ preferably not higher than 0.5 g/cm$^3$ but not lower than 0.1 g/cm$^3$, under the condition that the mean density of the porous material portions is lower than the mean density of material of the partitions.

The porous material portions generally occupy 10 to 90 volume % of the composite material sheet, and a mean pore size generally is in the range of 0.1 to 50 μm.

The porous material portions are preferably produced from organic polymer material such as cellulose derivative (e.g., cellulose acetate or nitrocellulose), polyamide (nylon, e.g., 6-nylon or 6,6-nylon), fluoropolymer (e.g., polytetrafluoroethylene or polyvinylidene fluoride), polyvinyl chloride, polycarbonate, polysulfone, or polyether sulfone or inorganic material such as ceramics. These materials can be employed in combination, if desired.

The arrangement and shapes of the openings of the porous material portions 23 are not limited to the grid arrangement and round openings illustrated in FIG. 4. Other arrangements and shapes can be adopted.

Figure 6:
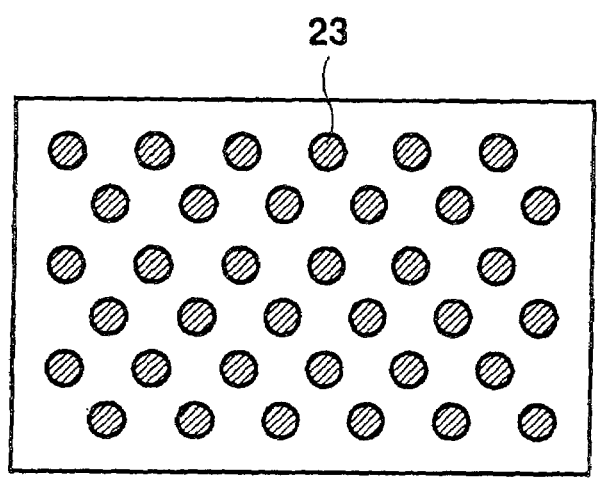
FIG. 6 is a plane view showing a variation of pattern of arrangement of the porous material portions.

FIG. 6 is a plane view showing a variation of pattern of the arrangement of porous material portions. In FIG. 6, a group of the porous material portions are composed of plural rows of porous material portions which are arranged with sequential shift of the positions of the porous material portions.

Figure 7:
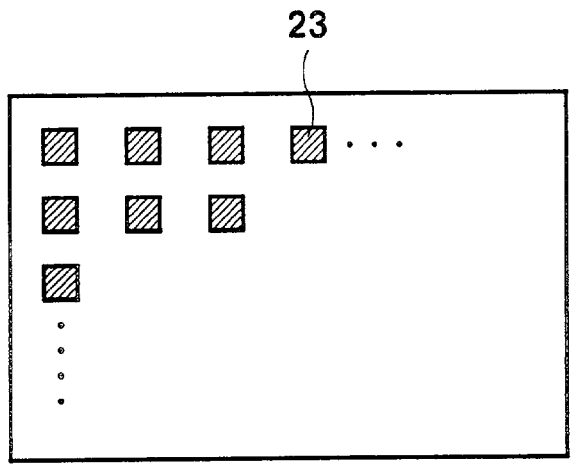
FIG. 7 is a plane view showing the porous material portions which have openings of a different shape.

FIG. 7 is a plane view showing a variation of the shape of opening of the porous material portion. In FIG. 7, the opening of the porous material portion 23 takes a shape of square.

Alternatively, the porous material portions are arranged at random on the composite material sheet, and the shape of opening can be oval or polygonal such as hexagonal.

The composite material sheet can be prepared by the following process.

First, a substrate having a desired partition pattern is produced using the aforementioned partition material. For instance, if the partition material is metal, the metal is electrocast on an appropriate mould to produce a substrate having a large number of openings. If the partition material is plastic resin, the plastic resin is dissolved in a solvent to give a resin solution and the resin solution is casted and dried to give a resin sheet. The resin sheet is etched by lithography such as dry etching or laser processing utilizing LIGA process or excimer laser, to give the desired substrate having a large number of openings. If the partition material is ceramics material, a slurry of ceramics material are molded and pressed to give a ceramic sheet. The ceramic sheet is then etched by laser or other means so that the ceramic sheet can have a large number of openings.

Separately, the material for the porous material portion is dissolved or dispersed in an appropriate solvent to give a solution or dispersion. The solution or dispersion is then placed in each opening of the substrate produced above, and dried to give a porous material portion in each opening. In the case using polyamide which shrinks in contact with water, a non-aqueous polyamide solution is first placed in the openings and dried to produce membrane and subsequently thus produced sheet is immersed in an aqueous medium to produce micro-pores in the polyamide membrane in each opening. In the case. using ceramics, ceramic particles having micro-pores are dispersed, placed in the openings, and dried.

Alternatively, an independently prepared porous material sheet can be placed on the substrate having a large number of openings under pressure so that portions of the porous material sheet are pushed into the openings of the substrate.

Thus, a composite material sheet comprising a substrate having a large number of openings and porous material portions placed in the openings such as that illustrated in FIGS. 4 and 5 is prepared.

In the detection process of the invention, a simple porous sheet can be employed in place of the composite material sheet. The simple porous sheet can be the one which is employed as a macro-array sheet in the known method for detecting substances originating from living body or its analogues. The simple porous sheet can be prepared from organic polymer material such as cellulose derivative (e.g., cellulose acetate or nitrocellulose), polyamide (nylon, e.g., 6-nylon or 6,6-nylon), fluoropolymer (e.g., polytetrafluoroethylene or polyvinylidene fluoride), polyvinyl chloride, polycarbonate, polysulfone, or polyether sulfone or inorganic material such as ceramics. These materials can be employed in combination, if desired.

The probe molecules to be fixed on the composite material sheet can be polynucleotides or oligonucleotides which are conventionally employed for the conventional macro-array sheet. For instance, cDNA (complementary DNA synthesized using mRNA as template), a portion of cDNA, polynucleotide prepared by multiplation utilizing PCR method such as EST (PCR product), and synthesized oligonucleotide can be mentioned. Alternatively, an artificial nucleic acid prepared from DNA by changing the phosphodiester bondings to peptide bondings, namely, PNA, or its derivative. Otherwise, proteins such as antigens or antibodies which can pertain in immunological specific binding reaction can be employed as probe molecules.

Examples of the combinations between the probe molecule and target molecule include DNA (or DNA fragment, or oligo DNA) and DNA, DNA and RNA, PNA and DNA (or RNA), PNA and PNA, antigen and antibody, and abidine and biotin.

The process for detecting substances originating from living body, their fragments, or their duplicate products is generally carried out by the following steps:

preparing the composite material sheet to each porous material portion of which a group of probe molecules are attached, or the porous material sheet to which a group of probe molecules are attached in the predetermined positions;

bringing sample molecules having a radioactive label in the presence of water into contact with the prepared composite material sheet, whereby target molecule (contained in the sample molecules) complementary to the probe molecules in the sample molecules are fixed by hybridization to the probe molecules;

removing unfixed sample molecules from the composite material sheet;

keeping the last-mentioned composite material sheet in contact with a stimulable phosphor sheet so that the stimulable phosphor sheet can absorb and store radiation energy of the radioactive label coming from the fixed target molecules—autoradiography;

irradiating the stimulable phosphor sheet with a stimulating light, whereby the stimulable phosphor sheet releases stimulated emissions from the areas in which the radiation energy is stored;

detecting the stimulated emissions photoelectrically to obtain a series of electric signals; and processing the electric signals to detect the area to which the complementary target molecules are fixed.

Figure 8:
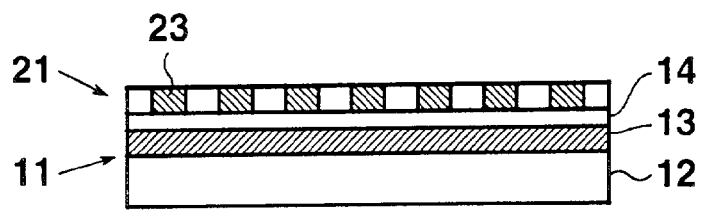
FIG. 8 illustrate a section of a laminate of a composite porous sheet and a stimulable phosphor sheet.

The autoradiography is generally performed by placing, as illustrated in FIG. 8, on the stimulable phosphor sheet of the invention 11 a composite material sheet 21 (or a simple porous material sheet) having complementary radioisotope-labeled target molecules by hybridization, at a temperature in the range of 0 to 30° C., for one hour to 120 hours.

Figure 9:
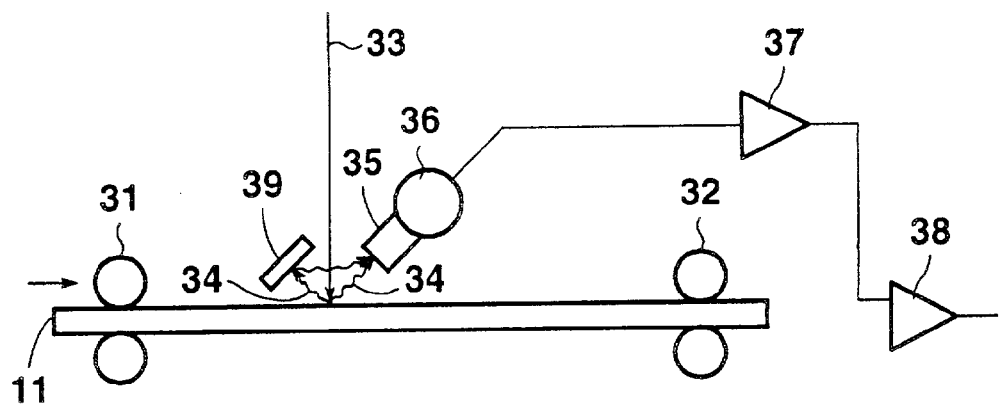
FIG. 9 illustrates an apparatus for reproducing a radiation image from a stimulable phosphor sheet which has been subjected to autoradiographic procedure.

The typical radiation image reproducing procedure is illustrated in FIG. 9.

In FIG. 9, a radiation image storage panel 11 is transferred in the direction of arrow, by means of a pair of rollers 31. On the storage panel 11 is applied a stimulating light 33. A stimulated emission 34 is directly detected by a light detecting means 35 or indirectly detected after reflection on a mirror 39. In the photoelectric conversion means 36, the stimulated emission 34 is converted into a series of electric signals, which are then transmitted to a multiplier 37 and further processed in a processor 38.

In the processor 38, a series of electric signals supplied from the multiplier 37 are subjected to appropriate processing such as addition or deduction depending on the nature of the desired radiation image or the characteristics of the employed stimulable phosphor sheet. Thus processed electric signals are then output as a set of image signals.

The set of image signals are subsequently reproduced on a display (e.g., CRT), recorded on an appropriate storage device such as photographic film, optical disc, or magnetic disc.

The invention is further described by the following non-limitative examples.

EXAMPLE 1

(1) Production of Substrate Having Fine Through-Holes

A substrate having a large number of small through-holes were produced by electrocasting nickel metal on a mould. The produced substrate had a size of 40 mm×60 mm, a thickness of 0.2 mm, 2,400 through-holes, and a density (number per $cm^2$) of through-holes of 100/$cm^2$. The through-hole has an round opening of 0.07 $mm^2$. A mean density of the substrate (corresponding to mean density of the partitions) was 8.8 g/$cm^3$.

(2) Production of Porous Material Portions

To a mixture of 83 wt. % of formic acid and 2 wt. % of water was added 15 wt. % of nylon 6, and the resulting mixture was well mixed at room temperature for 3 hours. The mixture was further mixed at 50° C. for one hour to give a polymer solution. The polymer solution was then cooled to reach room temperature. The cooled polymer solution was poured into the through-holes of the substrate. The poured solution was dried to give a membrane in each through-hole. The substrate having a membrane in each through-hole was immersed into an aqueous formic acid solution (formic acid concentration: 20 wt. %), so that a large number of micropores were produced in each membrane. Thus, a composite material sheet composed of a nickel substrate having partitions and porous nylon-6 membrane portions (such as that illustrated in FIGS. 4 and 5) was produced.

(3) Evaluation of Autoradiographic Process

To each porous nylon-6 membrane portion of the composite material sheet were attached single-stranded nucleic acid fragments (probe molecules) according to the well known method. The composite material sheet was then immersed in a solution of separately prepared radioactively labeled single-stranded nucleic acids (target molecules) complementary to the probe molecules, for carrying out hybridization.

The composite material sheet was taken out of the solution, washed with water, and dried. The composite material sheet was then placed on a stimulable phosphor sheet (stimulable phosphor BaFBr:Eu, thickness of support 100 μm, thickness of phosphor layer 10 μm, thickness of protective layer 3 μm) for performing autoradiography at room temperature. In the autoradiographic procedure, the composite material sheet was placed on the stimulable phosphor sheet in such manner that the positions of the porous material portions having fixed target molecules therein face the stimulable phosphor layers, in the manner described in FIG. 8.

The stimulable phosphor sheet subjected to autoradiography was then subjected to radiation image storing and reproducing procedure, using an apparatus such as that illustrated in FIG. 9. There was obtained a radiation image indicating the positions of porous membrane areas in which the radioactively-labeled target molecules were placed by hybridization with the probe molecules, with high sensitivity and high resolution.

What is claimed is:

1. A process for detecting complementary nucleic acid fragments which comprises the steps of:

preparing a composite material sheet, wherein said composite material sheet comprises partitions two-dimensionally extending on a sheet plane to form plural fine sections on the sheet plane, and a porous material portion placed in each fine section, wherein a group of probe molecules are attached to each porous material portion;

bringing radioactively labeled sample substances in a liquid phase, into contact with the prepared composite material sheet, whereby target substances among the sample substances are fixed to the probe molecules by a specific biochemical reaction;

removing unfixed sample substances from the composite material sheet;

keeping the composite material sheet having sample substances fixed by a specific biochemical reaction in contact with a stimulable phosphor sheet, wherein the stimulable phosphor sheet has a phosphor layer which has a thickness of 5 to 50 μm and which contains a stimulable phosphor in an amount of 10 to 140 g/$m^2$, whereby the stimulable phosphor layer absorbs and stores radiation energy of the radioactive label coming from the fixed target substances;

irradiating the stimulable phosphor sheet with a stimulating light, whereby the phosphor layer in which the radiation energy is stored releases stimulated emissions;

detecting the stimulated emissions photoelectrically to obtain a series of electric signals; and processing the electric signals to detect dots in which the target substances are present.

2. The process of claim 1, wherein the probe molecules are nucleic acid fragments, and the target substances are nucleic acid fragments complementary to the probe molecules.

3. The process of claim 1, wherein the probe molecules are single-stranded nucleic acid fragments and the target substances in the sample substances are single-stranded nucleic acid fragments complementary to the probe molecules.

4. The process of claim 1, wherein the partitions of the composite material sheet are made of material having a mean density of not lower than 0.6 g/cm$^3$ and the porous material portions have a mean density of not higher than 1.0 g/cm$^3$, provided that the mean density of material of the partitions is higher than the mean density of the material of the porous material portions.

5. The process of clam 1, wherein at least one of an upper and a lower surface of the porous material portions in the composite material sheet retracts from an upper or a lower surface of adjoining partitions on the sheet plane.

* * * * *